United States Patent [19]
Tackett et al.

[11] Patent Number: 5,117,016
[45] Date of Patent: May 26, 1992

[54] METHOD FOR OBTAINING A STIGMASTEROL ENRICHED PRODUCT FROM DEODORIZER DISTILLATE

[75] Inventors: Tommy L. Tackett, Batesville, Ak.; Charles A. McCombs, Kingsport, Tenn.

[73] Assignee: Eastman Kodak Company, Rochester, N.Y.

[21] Appl. No.: 699,021

[22] Filed: May 13, 1991

[51] Int. Cl.$^5$ .............................................. C07J 75/00
[52] U.S. Cl. ................................................... 552/545
[58] Field of Search ......................................... 552/545

[56] References Cited

U.S. PATENT DOCUMENTS

| | | | |
|---|---|---|---|
| 2,704,764 | 3/1955 | Mattikow et al. | 260/333 |
| 2,729,655 | 1/1956 | Miller et al. | 260/397.25 |
| 2,843,610 | 7/1958 | Brown et al. | 260/397.25 |
| 2,870,176 | 1/1959 | Stern et al. | 260/397.25 |
| 4,044,031 | 8/1977 | Johansson et al. | 552/545 |

*Primary Examiner*—Howard T. Mars
*Assistant Examiner*—Kimberly J. Kestler
*Attorney, Agent, or Firm*—Thomas R. Savitsky; Betty J. Deaton; William P. Heath, Jr.

[57] ABSTRACT

A method for obtaining a stigmasterol enriched product from esterified deodorizer distillate by use of a particular solvent system. The solvent system contains water, a $C_1$ to $C_6$ alcohol such as methanol, and a non-polar solvent such as heptane.

26 Claims, No Drawings

METHOD FOR OBTAINING A STIGMASTEROL ENRICHED PRODUCT FROM DEODORIZER DISTILLATE

FIELD OF INVENTION

This invention concerns use of a particular solvent system for obtaining a stigmasterol enriched product from esterified deodorizer distillate.

BACKGROUND OF THE INVENTION

During the processing of vegetable oils, such as soybean oil or corn oil, such oils are usually subjected to a high temperature steam distillation step under high vacuum to distill off volatile material which produces undesirable flavors and odors in the oil. This operation is usually referred to as deodorization. The materials causing such flavors and odors are largely unidentified, but the distillates from the deodorization ("deodorizer distillate") contains substantial quantities of fatty materials including free fatty acids, glycerides of fatty acids and unsaponifiables such as sterols and tocopherols. The sterol portion of the deodorizer distillate contains a mixture of sterols such as stigmasterol, sitosterol, and campesterol. Of the sterols, stigmasterol is particularly valuable as an intermediate for the preparation of certain pharmaceuticals such as sex hormones, cortisone, and the like.

Several processes for purification of sterols from deodorizer distillate or related materials are known in the art. For example, U.S. Pat. No. 2,704,764 discloses a general process for transesterification of deodorizer distillate, the esterification of fatty acids, and the isolation of sterols using an alcohol solvent. U.S. Pat. No. 2,729,655 discloses recovering sterols from deodorizer distillate by dissolving the methyl esters in a petroleum hydrocarbon solvent and saturating the resulting solution with water to precipitate the sterols. U.S. Pat. No. 2,843,610 discloses treating deodorizer distillate by saponification and esterification followed by crystallization of the sterols with acetone, methanol and water. Finally, U.S. Pat. No. 2,870,176 discloses recrystallization of a phytosterol concentrate from anhydrous heptane which provides an enrichment of the stigmasterol content.

It would be highly desirable to have a process which improves upon the prior art by providing a product with improved yield and purity of stigmasterol from deodorizer distillate.

SUMMARY OF THE INVENTION

We have surprisingly discovered a crystallization process which results in improved yield and/or purity of stigmasterol from deodorizer distillate. The novel process of the present invention capitalizes upon a unique solvent system for recrystallization. More specifically, the present invention is directed to a method for isolating a stigmasterol material from deodorizer distillate, said method comprising:

(A) esterifying deodorizer distillate to form an esterified deodorizer distillate containing fatty acid esters, (B) crystallizing the esterified deodorizer distillate from a solvent system comprising:
(a) a $C_1$ to $C_6$ alcohol,
(b) water, and
(c) a non-poplar solvent, to form a precipitate enriched with stigmasterol.

DETAILED DESCRIPTION OF THE INVENTION

It is preferred that step (B) of the method of the invention is followed by the following additional step:

(C) washing the enriched precipitate with a $C_5$ to $C_{10}$ hydrocarbon solvent.

The optional washing step improves the total sterol purity by removing or rinsing away impurities such as waxy, gum-like material. Additionally, the optional washing step may also enhance the stigmasterol content of the product. This washing step is a rinsing step and is not a second recrystallization. It is an advantage of the present invention that high levels of sterol and stigmasterol purity can be achieved by a single crystallization optionally followed by a washing step rather than by use of multiple crystallizations. Examples of $C_1$ to $C_{10}$ hydrocarbon solvents for use in the washing step include pentane, hexane, heptane, and the like. The most preferred solvent is heptane.

The non-poplar solvent for use in step (B) of the present invention can be a $C_5$ to $C_{10}$ hydrocarbon or it can be the lower alkyl ester of fatty acids formed during the esterification step (i.e., step (A)). As used herein the term "lower alkyl" means alkyl groups of one to six carbon atoms such as methyl or ethyl.

Examples of hydrocarbon non-poplar solvents include pentane, hexane, heptane, and the like. The most preferred hydrocarbon non-poplar solvent is heptane.

The non-poplar environment is important for obtaining the stigmasterol enriched product of the invention. For example, if acetone is used in place of a non-poplar solvent such as heptane, the stigmasterol content of the product is substantially reduced.

In the method of the invention said deodorizer distillate typically comprises about 2 to about 80 weight % of total sterols of which about 10 to about 19 weight % is stigmasterol; and the stigmasterol enriched precipitate comprises about 80 to about 96 weight % total sterols of which about 20 to about 25 weight % is stigmasterol. A more typical deodorizer distillate comprises about 10 to about 15 weight % of total sterols of which about 17 to about 19 weight % is stigmasterol; and a more typical stigmasterol enriched precipitate comprises about 85 to about 96 weight % (preferably about 92 to about 96 weight %) total sterols of which about 20 to about 25 weight % (preferably about 22 to about 25 weight %) is stigmasterol.

The $C_1$ to $C_6$ alcohol for use in the method of the invention is preferably an alkanol such as methanol, ethanol, isopropanol and the like. The most preferred alcohol is methanol.

In the method of the invention it is also preferred that prior to performing step (A) the following step is performed:

(A') saponifying deodorizer distillate to form a saponified deodorizer distillate containing fatty acids.

The saponification step (i.e., step (A')) can be carried out by conventional means known in the art. For example, it is preferred that step (A') is carried out at a temperature of about 50° C. to about 55° C. It is also preferred that the saponification of step (A') is carried out by contacting the deodorizer distillate with an alkaline earth hydroxide in the presence of a $C_1$ to $C_6$ alkanol solvent. A preferred alkaline earth hydroxide is NaOH, a preferred strong mineral acid is HCl, and a preferred alkanol is methanol.

The esterification step (step (A)) also can be carried out by conventional means known in the art. For example, a temperature range of about 50° C. to about 55° C. can be employed. The esterification of step (A) is typically carried out by contacting the saponified deodorizer distillate (i.e., the product of step (A′)) with a strong mineral acid (e.g., HCl) in the presence of a $C_1$ to $C_6$ alkanol solvent (e.g., methanol).

A typical product produced by step (A) contains the following:
(i) about 50 to about 70 weight % of alkyl esters (preferably methyl esters) of fatty acids,
(ii) about 12 to about 15 weight % of sterols, and
(iii) about 15 to about 38 weight % of a non sterol, non ester residue.

For step (B) of the method of the invention a typical temperature range is about −20° C. to about 50° C. In the method of the invention it is preferred wherein the solvent system for step (B) consists essentially of about 2 to about 80 weight % of component (a); about 2 to about 80 weight % of component (b); and about 10 to about 90 weight % of component (c); more preferred is wherein said solvent system consists essentially of about 3 to about 35 weight % of component (a); about 3 to about 6 weight % of component (b); and about 60 to about 90 weight % of component (c).

A typical weight ratio of esterified deodorizer distillate:solvent system for step (B) of the method of the invention is about 1:10 to about 10:1.

For the method of the invention it is preferred wherein the yield of total sterols in the stigmasterol enriched precipitate is at least about 80% and the yield of stigmasterol in said precipitate is at least about 95%.

A preferred method of the invention can be described as a method for isolating a stigmasterol material from deodorizer distillate, said method comprising:

(A′) saponifying deodorizer distillate to form a saponified deodorizer distillate containing fatty acids, (A) esterifying the saponified deodorizer distillate to form an esterified deodorizer distillate containing fatty acid esters, (B) crystallizing the esterified deodorizer distillate from a solvent system comprising:
(a) a $C_1$ to $C_6$ alcohol,
(b) water, and
(c) a non-poplar solvent selected from a $C_5$ to $C_{10}$ hydrocarbon, the lower alkyl esters of fatty acids, or a mixture thereof, to form a precipitate enriched with stigmasterol, and (C) washing the stigmasterol enriched precipitate with a $C_5$ to $C_{10}$ hydrocarbon solvent.

The following example is to illustrate the invention but should not be interpreted as a limitation thereon.

EXAMPLE

Esterified deodorizer distillate (456 g, stigmasterol=3.54%, total sterols=15.29%) was dissolved in 300 mL of heptane, 20 mL of methanol and 20 mL of water. The resulting solution was cooled to 5° C., held for one hour and the insoluble sterols were filtered. The crude cake was further washed with 3×50 mL of heptane to remove tocopherols from the wet cake, and then dried in a 50° C. oven. The isolated cake weighed 58.3 g and assayed for 24.7% stigmasterol and 96.1% free sterols. The stigmasterol yield is calculated to be 95.4%, and the sterol yield is 83.9%.

The invention has been described in detail with particular reference to preferred embodiments thereof, but it will be understood that variations and modifications can be effected within the spirit and scope of the invention.

We claim:

1. A method for isolating a stigmasterol material from deodorizer distillate, said method comprising:
   (A) esterifying deodorizer distillate to form an esterified deodorizer distillate containing fatty acid esters,
   (B) crystallizing the esterified deodorizer distillate from a solvent system comprising:
   (a) a $C_1$ to $C_6$ alcohol,
   (b) water, and
   (c) a non-poplar solvent, to form a precipitate enriched with stigmasterol.

2. The method of claim 1 including the additional step of:
   (C) washing the enriched precipitate with a $C_5$ to $C_{10}$ hydrocarbon solvent.

3. The method of claim 1 wherein prior to performing step (A) the followinq step is performed:
   (A′) saponifyinq deodorizer distillate to form a saponified deodorizer distillate containing fatty acids.

4. The method of claim 1 wherein said non-polar solvent is a $C_5$ to $C_{10}$ hydrocarbon.

5. The method of claim 1 wherein said non-polar solvent is the lower alkyl ester of fatty acids.

6. The method of claim 1 wherein said $C_1$ to $C_6$ alcohol is methanol.

7. The method of claim 4 wherein said $C_1$ to $C_6$ alcohol is methanol.

8. The method of claim 5 wherein said $C_1$ to $C_6$ alcohol is methanol.

9. The method of claim 4 wherein said $C_5$ to $C_{10}$ hydrocarbon is heptane.

10. The method of claim 7 wherein said $C_5$ to $C_{10}$ hydrocarbon is heptane.

11. The method of claim 1 wherein said deodorizer distillate comprises about 2 to about 80 weight % of total sterols of which about 10 to about 19 weight % is stigmasterol; and said enriched precipitate comprises about 80 to about 96 weight % total sterols of which about 20 to about 25 weight % is stigmasterol.

12. The method of claim 1 wherein said deodorizer distillate comprises about 10 to about 15 weight % of total sterols of which about 17 to about 19 weight % is stigmasterol; and said enriched precipitate comprises about 85 to about 96 weight % total sterols of which about 20 to about 25 weight % is stigmasterol.

13. The method of claim 2 wherein the yield of total sterols in said stigmasterol enriched precipitate is at least about 80% and the yield of stigmasterol in said precipitate is at least about 95%.

14. The method of claim 1 wherein the weight ratio of esterified deodorizer distillate:solvent system for step (B) is about 1:10 to about 10:1.

15. The method of claim 2 wherein step (B) is carried out at a temperature of about −20° C. to about 50° C., step (A) is carried out at a temperature of about 50° C. to about 55° C., and step (A′) is carried out at a temperature of about 50° C. to about 55° C.

16. The method of claim 1 wherein said solvent system for step (B) consists essentially of about 2 to about 80 weight % of component (a); about 2 to about 80 weight % of component (b); and about 10 to about 90 weight % of component (c).

17. The method of claim 1 wherein said solvent system consists essentially of about 3 to about 35 weight % of component (a); about 3 to about 6 weight % of component (b); and about 60 to about 90 weight % of component (c).

18. The method of claim 2 wherein said $C_5$ to $C_{10}$ hydrocarbon used for washing is heptane.

19. The method of claim 3 wherein the saponification of step (A') is carried out by contacting the deodorizer distillate with an alkaline earth hydroxide in the presence of a $C_1$ to $C_6$ alkanol solvent; and the esterification of step (A) is carried out by contacting the saponified deodorizer distillate with a strong mineral acid in the presence of a $C_1$ to $C_6$ alkanol solvent.

20. The method of claim 19 wherein the alkaline earth hydroxide is NaOH, the strong mineral acid is HCl, and the $C_1$ to $C_6$ alkanol is methanol.

21. The method of claim 3 wherein said esterified product produced in step (A) and used in step (F) consists essentially of
   (i) about 50 to about 70 weight % of alkyl esters of fatty acids,
   (ii) about 12 to about 15 weight % of sterols, and
   (iii) about 15 to about 38 weight % of a non sterol, non ester residue.

22. A method for isolating a stigmasterol material from deodorizer distillate, said method comprising:
   (A') saponifying deodorizer distillate to form a saponified deodorizer distillate containing fatty acids,
   (A) esterifying the saponified deodorizer distillate to form an esterified deodorizer distillate containing fatty acid esters,
   (B) crystallizing the esterified deodorizer distillate from a solvent system comprising:
      (a) a $C_1$ to $C_6$ alcohol,
      (b) water, and
      (c) a non-poplar solvent selected from a $C_5$ to $C_{10}$ hydrocarbon, the lower alkyl esters of fatty acids, or a mixture thereof, to form a precipitate enriched with stigmasterol, and
   (C) washing the stigmasterol enriched precipitate with a $C_5$ to $C_{10}$ hydrocarbon solvent.

23. The method of claim 22 wherein the $C_1$ to $C_6$ alcohol is methanol and the $C_5$ to $C_{10}$ hydrocarbon for steps (B) and (C) is heptane.

24. The method of claim 22 wherein the yield of total sterols in said stigmasterol enriched precipitate is at least about 80% and the yield of stigmasterol in said precipitate is at least about 95%.

25. The method of claim 24 wherein said deodorizer distillate comprises about 2 to about 80 weight % of total sterols of which about 10 to about 19 weight % is stigmasterol; and said enriched precipitate comprises about 80 to about 96 weight % total sterols of which about 20 to about 25 weight is stigmasterol.

26. The method of claim 24 wherein said deodorizer distillate comprises about 10 to about 15 weight % of total sterols of which about 17 to about 19 weight % is stigmasterol; and said enriched precipitate comprises about 92 to about 96 weight % total sterols of which about 22 to about 25 weight % is stigmasterol.

* * * * *

UNITED STATES PATENT AND TRADEMARK OFFICE
CERTIFICATE OF CORRECTION

PATENT NO. :   5,117,016
DATED      :   May 26, 1992
INVENTOR(S):   Tommy L. Tackett et al.

It is certified that error appears in the above-identified patent and that said Letters Patent is hereby corrected as shown below:

Column 4, line 5 (Claim 1, line 1), after "from", ---sterols present in--- should be inserted.

Column 5, line 25 (Claim 22, line 2), between "from" and "deodorizer", ---sterols present in--- should be inserted.

Column 6, line 23 (Claim 25, line 6), between "weight" and "is" ---%--- should be inserted.

Signed and Sealed this

Twenty-fourth Day of August, 1993

Attest:

BRUCE LEHMAN

Attesting Officer        Commissioner of Patents and Trademarks